(12) United States Patent
Farber

(10) Patent No.: US 8,110,080 B1
(45) Date of Patent: Feb. 7, 2012

(54) METHOD FOR IMPROVING PERFORMANCE AND LONGEVITY OF SOLID ELECTROLYTE GAS SENSOR

(75) Inventor: Boris Farber, Solon, OH (US)

(73) Assignee: BJR Sensors, LLC, Solon, OH (US)

( * ) Notice: Subject to any disclaimer, the term of this patent is extended or adjusted under 35 U.S.C. 154(b) by 521 days.

(21) Appl. No.: 12/327,163

(22) Filed: Dec. 3, 2008

Related U.S. Application Data

(63) Continuation-in-part of application No. 10/843,993, filed on May 13, 2004, now abandoned.

(51) Int. Cl.
 *G01N 27/26* (2006.01)
(52) U.S. Cl. ........ 204/425; 204/426; 204/427; 204/428; 205/766
(58) Field of Classification Search .................. 204/426, 204/427, 428, 425; 205/782, 782.5, 783, 205/783.5, 784, 785
See application file for complete search history.

(56) References Cited

U.S. PATENT DOCUMENTS

| | | | | |
|---|---|---|---|---|
| 4,639,305 | A * | 1/1987 | Shibata et al. | 204/426 |
| 6,562,212 | B2 * | 5/2003 | Katafuchi et al. | 204/427 |

* cited by examiner

*Primary Examiner* — Bruce Bell
(74) *Attorney, Agent, or Firm* — John D. Gugliotta, PE, Esq.

(57) ABSTRACT

A method is provided for activating a zirconia oxygen sensor which detects the oxygen concentration of an ambient atmosphere by means of a zirconia element that has a porous electrode formed on both sides of an impervious oxygen ion conductor. An electrical current is applied as a pulsed, square wave, direct current during heat up, heat soak, and cool down of the ionic conductor that is applied to ceramic substrate, thereby causing oxygen ions to flowing through the sensor body and pumping oxygen gas through the sensor electrodes, thus improving electrode porosity distribution.

16 Claims, 9 Drawing Sheets

Treated EGO sensor (after stability test at 600C) raw voltage output while subjected to oxygen step changes 10%-6%-4%-2%-1%-0.5%-1%-2%-4%-6%-10%(a).
Fit into Nernst equation (b).
Measurement error at each gas level (c.)

Untreated sensor raw voltage output while subjected to oxygen step changes
10%-6%-4%-2%-1%-0.5%-1%-2%-4%-6%-10%(a).
Fit into Nernst equation (b).
Measurement error at each gas level (c.)

Untreated EGO sensor (aged for 4 days at 600C) raw voltage output while subjected to oxygen step changes 10%-6%-4%-2%-1%-0.5%-1%-2%-4%-6%-10%(a).
Fit into Nernst equation (b).
Measurement error at each gas level (c.)

Untreated EGO sensor (aged for 4 days at 600C) raw voltage output while subjected to oxygen step changes 10%-6%-4%-2%-1%-0.5%-1%-2%-4%-6%-10%(a).
Fit into Nernst equation (b).
Measurement error at each gas level (c.)

Untreated EGO Sensor raw voltage output while subjected to oxygen step changes 10%-6%-4%-2%-1%-0.5%-1%-2%-4%-6%-10% (a).
Fit results into Nernst equation (b).
Measurement error at each gas level (c).

METHOD FOR IMPROVING PERFORMANCE AND LONGEVITY OF SOLID ELECTROLYTE GAS SENSOR

RELATED APPLICATIONS

The present application is a continuation-in-part of Application Ser. No. 10/843,993, filed on May 13, 2004 now abandoned. The present application incorporates all of the subject matter of that application as if fully rewritten herein.

BACKGROUND OF THE INVENTION

1. Field of the Invention

The present invention relates to a method of activating a zirconia oxygen sensor which detects the oxygen concentration of an ambient atmosphere by means of a zirconia element that has a porous electrode formed on both sides of an impervious oxygen ion conductor.

2. Description of the Related Art

The sensing element used in zirconia oxygen sensors is generally formed of a zirconia thimble having an inner and outer metal coating, usually platinum, to form an electrode. The electrode is then used to measure the differential oxygen concentration between the measured gas on the outside of the thimble, and a reference gas, usually atmospheric, on the inside of the thimble. By measuring the voltage between two electrodes, the differential oxygen concentration can be calculated.

Solid electrolyte oxygen sensors comprising of gas impermeable zirconia ceramic separating two conductive (Pt) electrodes are widely used for combustion control in power plants as well as in the exhaust of automotive internal combustion engines. For utilization of oxygen sensors for industrial combustion control, the sensor must demonstrate certain performance criteria, i.e. a typical relative accuracy of between 3-5% (or absolute accuracy of 0.1-0.2%), a response time of less than 10 seconds, and a life expectancy typically greater than 1 year.

Oxygen Sensors used for automotive applications (Exhaust Gas Oxygen (EGO)) usually require different set of performance criteria. Beginning with 1994 model year, automotive manufacturers have been required to implement on board diagnostic systems, which can diagnose and detect malfunctioning emission related components. These systems usually involve dual exhaust gas oxygen sensors. One sensor is placed directly behind engine exhaust, and a second sensor is placed downstream of the three-way catalyst. The exhaust gas oxygen sensor generates large (~800-1,000 mV) voltage outputs in response to cyclic fluctuations in air/fuel ratio about the stoichiometric point caused by closed loop fuel control of the engine.

Desirable characteristics of the oxygen sensor placed directly behind the engine for an optimum close-loop control of inlet air-fuel mixture are high voltage output, fast switching time and reasonably long longevity (>100,000 miles). A Second sensor is, placed behind the three-way catalytic converter and exhibits reduced voltage output due to an increase in excess oxygen present in the exhaust stream which reflects oxygen storage capacity of the catalyst thus allowing evaluation of the hydrocarbons conversion efficiency. It is known that the presently used method can detect only a very narrow range of catalyst efficiencies. Below 80-90% conversion efficiencies, the rear EGO sensor index tends to saturate and provides little monitoring capability.

This sensor can greatly benefit from possessing performance characteristics typical for industrial oxygen sensors, which can accurately measure excess oxygen directly—rather than extract excess oxygen values through elaborate and indirect data processing typical for dual exhaust gas oxygen sensors systems. However, elaborate and expensive manufacturing methods used for industrial oxygen sensors manufacturing makes direct implementation of these sensors in automotive market cost prohibitive.

In the related art is known several improvements, and drawbacks, in preparing the sensing element. For example, it is known that structures that improve the diffusion of oxygen through the sensor electrodes can increase the accuracy and longevity of the completed sensor, while impediments to oxygen diffusion decrease the accuracy or longevity of the completed sensor. Currently, the best known improvements to aid in the diffusion of oxygen through the sensor electrodes include: to somehow create a distributed "microporosity" throughout the sensor electrode to provide efficient channels for diffusion; and increasing zirconia-platinum adhesion to similarly lessen any interface resistance that can affect impedance. Alternately, if oxidizing conditions exist at the zirconia-platinum interface during manufacturing an oxide layer of platinum is known to form. This oxide layer contributes to weak platinum adhesion to the zirconia substrate, and increased interface resistance. Additionally, high temperatures, required for sensor manufacturing, lead to electrode sintering, causing imperviousness to gas oxygen, thus increasing sensor impedance and deteriorated performance Numerous attempts have been made to generate the foregoing improvements. For instance, U.S. Pat. No. 5,433,830, issued in the name of Kawai et al., discloses a method for activating a zirconia oxygen sensor by heating the zirconia sensor body and attached platinum coating assembly in a temperature-controlled furnace, while applying an alternating treating voltage. As a result, the treatment current flowing through the sensor can activate the sensor by causing physical changes to occur in the Pt electrodes, and improving electrode porosity. Applied voltage (generated current) was specifically limited to below the reduction potential to prevent reduction of zirconia (blackening). Bulk reduction of zirconia is indeed detrimental to its performance due to potential cracking. However, surface reduction of zirconia can be beneficial for oxygen sensor performance, since it removes the oxide layer from Pt and zirconia and allows direct contact between Pt and Zirconium metal. Metal to metal contact has much better adhesion in comparison with metal to oxide or oxide to oxide contacts. Therefore, even though this activation method is helpful, it is still limited in that the application of an alternating voltage is dependant on other conditions for performing the treatment of such as a comparatively small treating current and a comparatively high treating temperature.

U.S. Pat. No. 6,562,212 to Katafuchi et al. teaches a gas sensor element that is to be used in an oxygen sensor. In order to activate the electrode, the target gas electrode is first exposed to a reducing gas atmosphere at an elevated temperature of 400-900 C. Preferably, the temperature is kept at 700 C. The electrode is then connected to a voltage source circuit wherein AC voltage having the frequency greater than 1 Hz and amplitude between +/−0.1 and +/−5.0V is applied for 30 minutes. The reference fails to teach whether the voltage is applied during the time when the electrode is heating up to 700 C, or after the soaking period at that temperature. The present method can be distinguished from Katafuchi et al. in that square wave voltage of alternating polarity is applied to the electrode during the soaking period at a constant temperature, as well during the period when the electrode is being heated up or cooled down from a constant temperature.

Consequently, a need has been felt for providing a method for improving a platinum-zirconia oxygen sensor by improving platinum adhesion, increasing sensor electrode microporosity under treatment conditions that limit oxide formation at the platinum-zirconia interface.

SUMMARY OF THE INVENTION

In the present invention a new method for electrode pre-treatment is proposed involving low frequency AC Voltage/current treatment in the form of a square wave with the voltage amplitude above the voltage of zirconia reduction (V>2.4V) and treatment temperature being sufficiently high to assure current amplitude in excess of ~200 mA/cm2 for an industrial oxygen sensor and in excess of ~40 mA/cm2 for an automotive Exhaust Gas Oxygen Sensor. As demonstrated in the below examples, this method will allow further optimization of the automotive EGO sensors, improving their performance to the level compatible with commercial $O_2$ sensors used for industrial process control.

The present invention has been accomplished under these circumstances and has an object to provide a method of activating a zirconia oxygen sensor by which the sensing element can be activated effectively without causing oxidation conditions that can lead to oxide formation at the platinum-zirconia interface in the process of the activation treatment.

According to the present invention, activation treatment for a zirconia oxygen sensor is performed by applying alternating polarity, direct current/square wave voltage during heating, soak at the treatment temperature, and cooling of the sensor assembly. As a result of treatment current, oxygen ions are flowing through the sensor body, converts into oxygen gas at the zirconia/Pt interface and oxygen gas pumps through the sensor electrodes, thus improving electrode porosity distribution. Applied voltage is chosen higher than in previously known methods (greater than or equal to the zirconia reduction potential of +/−2.4V), causing surface reduction of zirconia and improving zirconia to Pt electrode adhesion and reducing overall sensor impedance. The upper limit for the applied voltage can vary depending upon the particular design of the sensor, but it is anticipated that the preferable voltage range should be +/−2.4-5.0V. Such range provides for a voltage that is higher than the zirconia reduction potential, but lower than voltage that would cause mechanical disintegration of zirconia. Voltages higher than 5.0V will create a discolored layer at the electrode surface. Cool down procedure is also different from the known method. Since Voltage pulses are continuously applied during cool down of the sensor from treatment temperature down to the typical temperature of sensor usage, oxide formation in Zirconia-Pt interface can be prevented.

If the sensor is to be used in an air-fuel ratio control or the like on an internal combustion engine, such a treatment can improve accuracy and longevity without significantly increasing cost.

Further, if the sensor is to be used for other applications where higher accuracies are required, such a treatment can create a sensor equivalent to other conventionally available alternatives at a significantly decreased cost.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
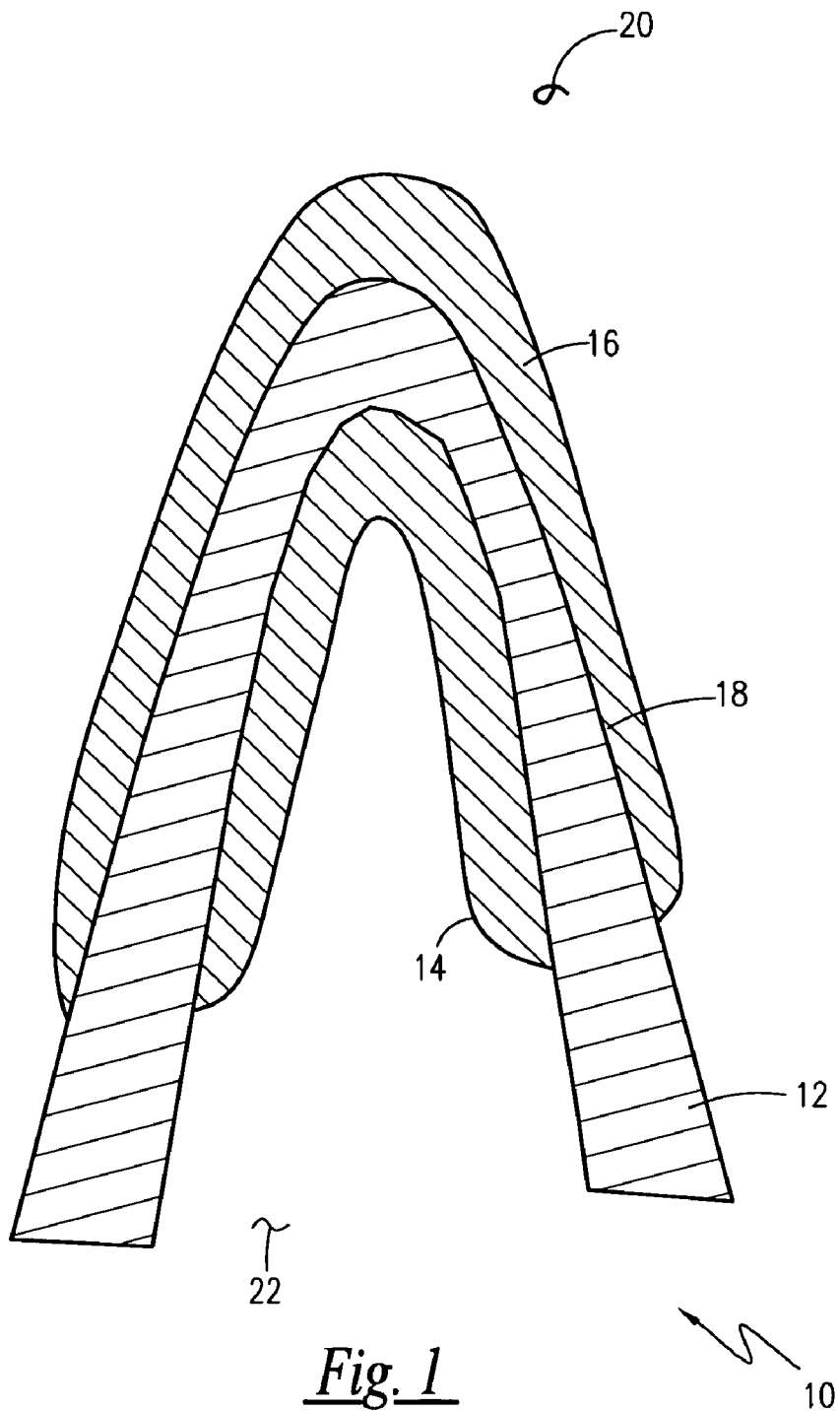
FIG. 1 is a simplified sectional view showing the construction of a zirconia oxygen sensor that is to be activated by an embodiment of the present invention.

In order to describe the complete relationship of the invention, it is essential that some description be given to the manner and practice of functional utility and description of FIG. 1, where a zirconia oxygen sensor 10 is shown. According to the present invention, the sensor 10 is generally formed of a zirconia thimble 12 having an inner platinum coating 14 and an outer platinum coating 16 to form an electrode. A zirconia-platinum interface 18 is formed at this boundary. The electrodes are then used to measure the differential oxygen concentration between the measured gas 20 on the outside of the thimble, and a reference gas 22, usually atmospheric, on the inside of the thimble 12. As such, it can be seen by one skilled in the art that a platinum coating on either surface can be replaced by another material, such as paladium or the like, to provide an electrode of slightly different properties for similar applications.

Figure 2:
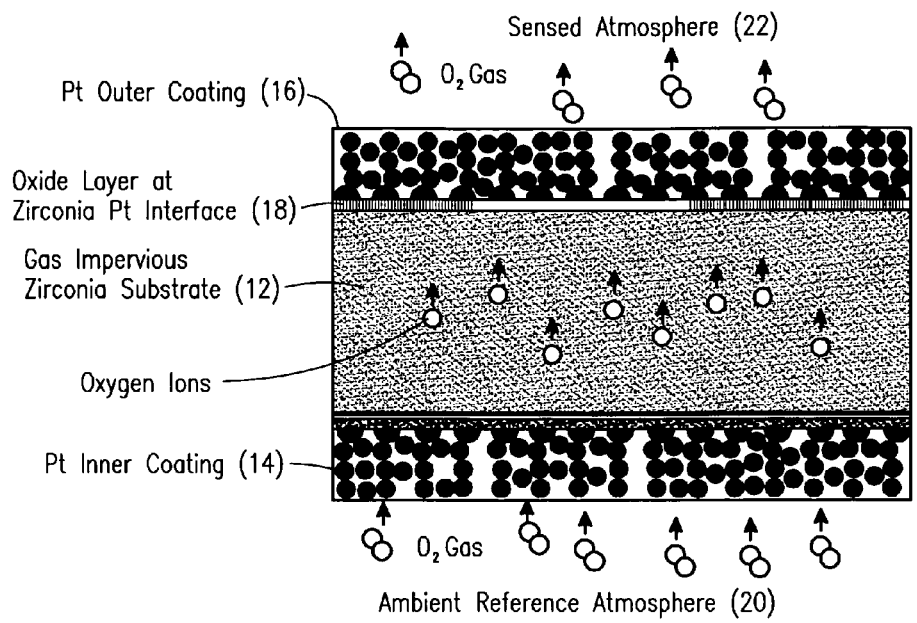
FIG. 2 is a simplified sectional view of FIG. 1 shown in greater scale of an untreated sensor.
Figure 3:
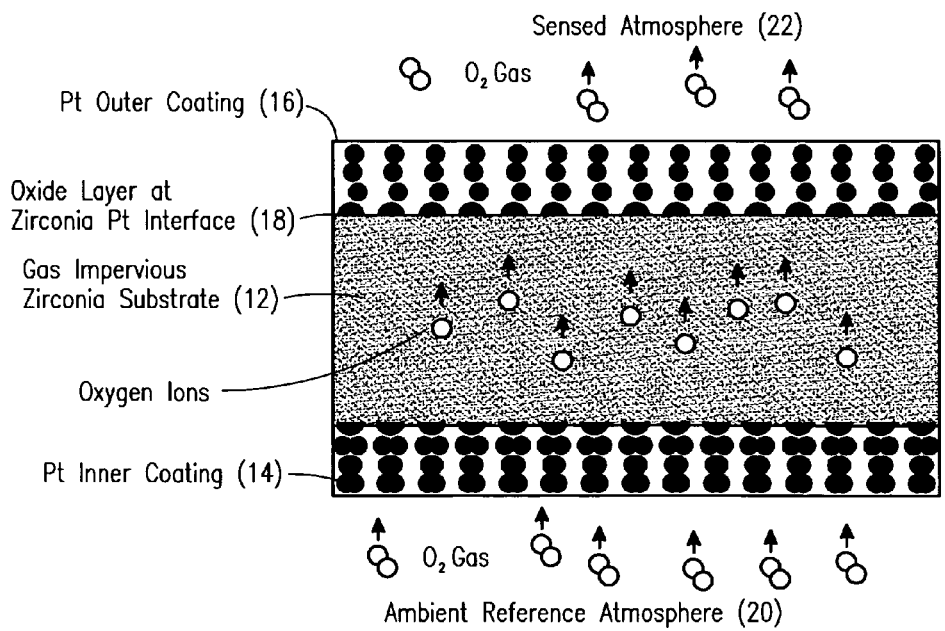
FIG. 3 is simplified a graphs showing typical desirable effects that are attained by performing an activation treatment on the A/F ratio sensor of FIG. 1 in accordance with the present invention.

As shown in greater detail in conjunction with FIG. 2, as manufactured an untreated oxygen sensor has poor electrode porosity (14 and 16) and an oxide interface layer (18) between Pt electrodes (14, 16) and zirconia substrate (12). Both these factors detrimentally affect sensor impedance and longevity. FIG. 3 demonstrates desired improvements in sensor element microstructure as a result of proposed activation treatment. Platinum electrodes have much better developed porosity allowing easy pass for oxygen gas diffusion to Pt/Zirconia interface and oxide layer is absent in Zirconia-Pt interface. Both these factors decrease overall sensor impedance and improve electrode adhesion to zirconia substrate.

Figure 4:
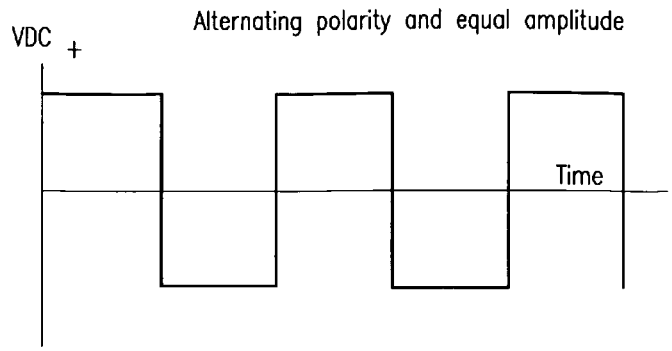
FIG. 4. is a schematic representation of treatment conditions.

Referring now to FIG. 4, when a voltage is applied between the electrodes of the sensing element, a current flows through the element and oxygen flows in a direction that opposes the current flow, namely, from the lower-potential electrode (cathode) towards the higher-potential electrode (positive electrode). By applying this voltage as a square wave direct current, this flow of oxygen through the sensor can be accomplished in a slow, controlled fashion, thereby forming an even distribution of micropores throughout the sensor electrodes. Thereafter, by applying a square wave direct current of an equal and opposite polarity, the flow of oxygen through the sensor is reversed, thereby forming these micropores in the opposite electrode into a more readily diffusable channel when the sensor is completed.

1. Example 1

Automotive EGO Sensors

According to one example of the preferred embodiment of the present invention for use with Automotive EGO Sensors, improved internal resistance stability was shown in a commercially available EGO sensor when it was treated with square wave voltage pulses with the amplitude of 2.6 volts and frequency of 0.2 Hertz. The sensor was heated up to 450 Celsius. At this temperature, square wave pulses were applied between working and reference electrodes. Under these pulses the sensor was heated up to 700° C. at 10 C/min, was held at 700° C. for at least 0.5 H, and cooled down to 450° C. under voltage pulses. Maximum current amplitude was ~40 mA/cm$^2$ at 700° C.

Following the above described voltage/current treatment, the sensor internal resistance was measured with AC Impedance Spectroscopy and its variation was monitored over several days while maintaining the sensing element temperature at 600° C. Variations in the sensor internal resistance was compared with untreated sensors.

Figure 5:
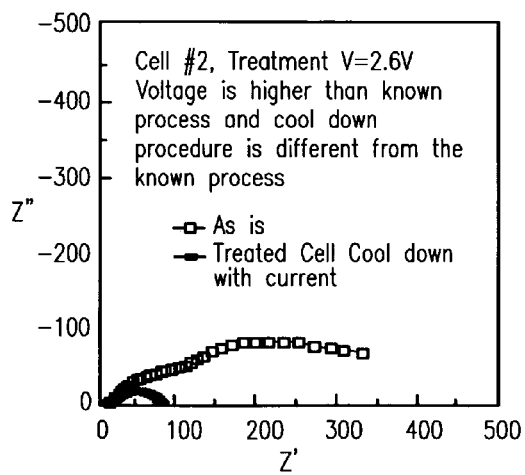
FIG. 5. shows the AC Impedance spectra of EGO sensor before and after treatment with proposed method according to preferred embodiment.

FIG. 5 shows AC Impedance spectra for a EGO sensor treated according to the preferred embodiment as described above. Sensor internal resistance was reduced from ~350 Ohms (for untreated sensor) down to ~80 Ohms for treated sensor.

Figure 6:
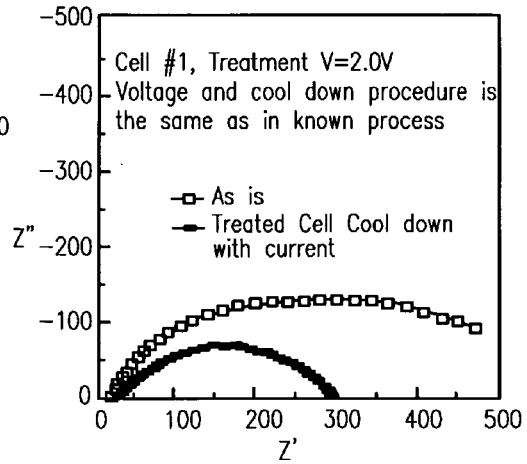
FIG. 6. shows AC Impedance spectra of EGO sensor before and after treatment with square wave voltage pulses according to known procedure.

FIG. 6 Shows AC Impedance spectra for an EGO sensor treated according to the known activation method. The applied Voltage V=2.0V was lower than the reduction potential for zirconia, and cool down from treatment temperature was performed without applied voltage pulses. Sensor resistance decreased as a result of the treatment (from ~500 Ohms) down to ~300 Ohms. However, attained final resistance was significantly higher than achieved with the proposed new treatment conditions (80 Ohms, see FIG. 5).

Figure 7:
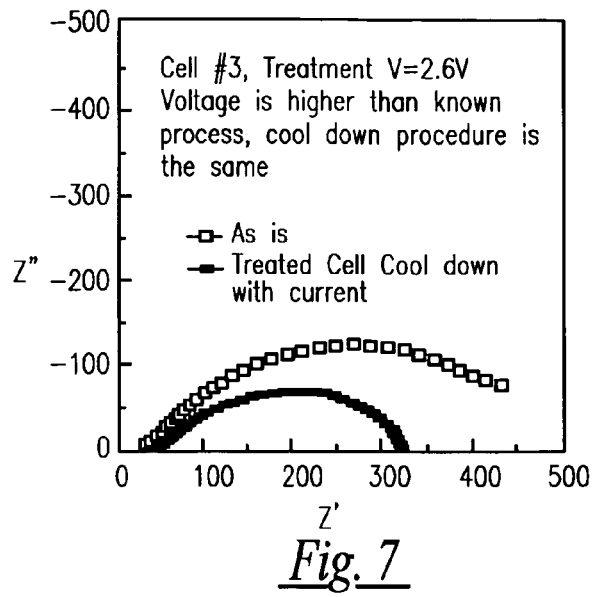
FIG. 7. shows AC Impedance spectra of EGO sensor before and after treatment with square wave voltage pulses according to certain aspects of known procedure.

FIG. 7. Shows AC Impedance spectra for EGO sensor treated according to certain aspects of the known activation method. Sensor was treated with high voltage (V=2.6 V), exceeding the reduction potential of zirconia, however cool down from treatment temperature was performed without applied voltage (as in the known activation method). Sensor resistance decreased as a result of the treatment (from ~400 Ohms) down to ~250 Ohms. However, the attained final resistance was still significantly higher than achieved with the proposed new treatment conditions (80 Ohms, see FIG. 5).

Comparison between FIGS. 5-7 clearly demonstrates that the proposed method of EGO sensor activation has significant advantages over the existing method, by allowing lowest resistance to be attained as a result of the treatment.

Figure 8:
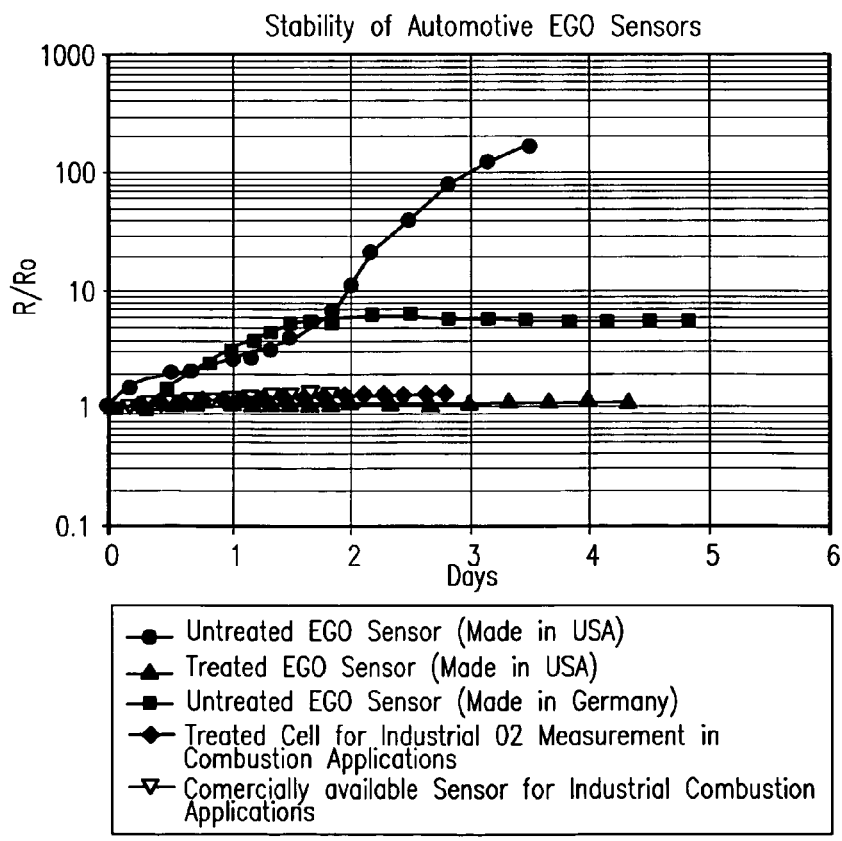
FIG. 8 shows the stability of automotive EGO and $O_2$ sensors for industrial combustion applications.

FIG. 8 shows treated and untreated sensor degradation curves. It is seen that relative the increase of the untreated sensor #1 internal resistance exceeded 200 times during 3.5 days. Untreated sensor #2 increased its resistance ~6 times during 5 days. The treated sensor increased its resistance by ~10% during the same annealing time.

Typical sensor performance deteriorates noticeably once its relative resistance changes more than 3 times. Extrapolation of the measured degradation curve indicates that a treated cell will remain operational for a period of more than a year. An untreated cell would show deteriorated performance after only several days in use.

2. Example 2

Treatment of Oxygen Sensors for Industrial Combustion Applications

A zirconia tube substrate was coated with platinum by using commercially available platinum inks. Electrodes were fired at ~1300° C. Following firing, electrodes were treated with a similar treatment as described above for EGO sensors. Voltage pulses with the amplitude V=2.6 V, and frequency=0.2 Hz. Sensor was heated up to 500° C. At this temperature, square wave pulses were applied between working and reference electrodes. Under these pulses the sensor was heated up to 900° C. at ~10 C/min, was held at 900° C. for at least 0.5 H, and cooled down to 500° C. under voltage pulses. Maximum current amplitude was ~200 mA/cm$^2$ at 900° C. Following the above described voltage/current treatment, the sensor internal resistance was measured with AC Impedance Spectroscopy and its variation was monitored over several days while maintaining sensing element temperature at ~600° C. Variations in the sensor internal resistance was compared with commercially available untreated sensors for oxygen monitoring in industrial combustion applications.

Results of the stability test for treated and untreated oxygen sensors are also shown in FIG. 8. Both sensors showed good stability over the test period.

3. Automotive EGO Sensors—Accuracy of Measurements

Figure 9:
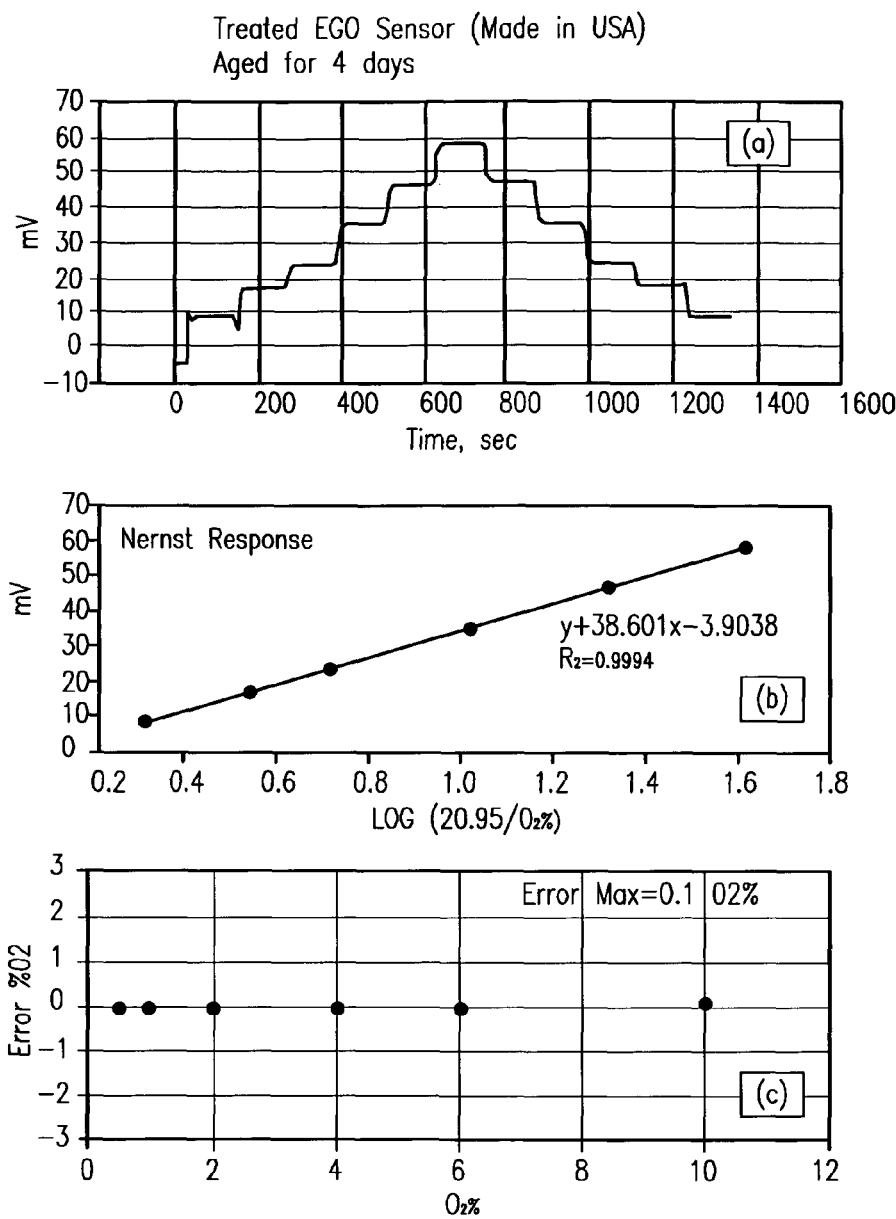
FIG. 9 shows the performance of the EGO sensor treated with square wave voltage, showing raw voltage output while subjected to oxygen step change.
Figure 10:
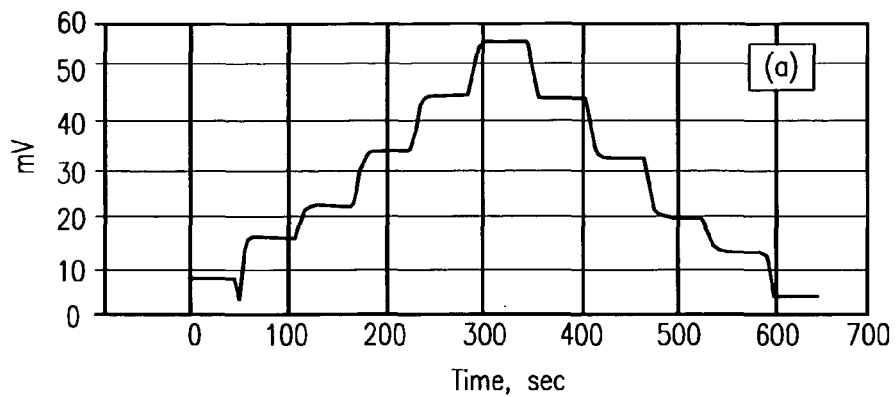
FIG. 10 shows the performance of untreated sensors of the type made in USA, showing raw voltage output while subjected to oxygen step change.
Figure 10:
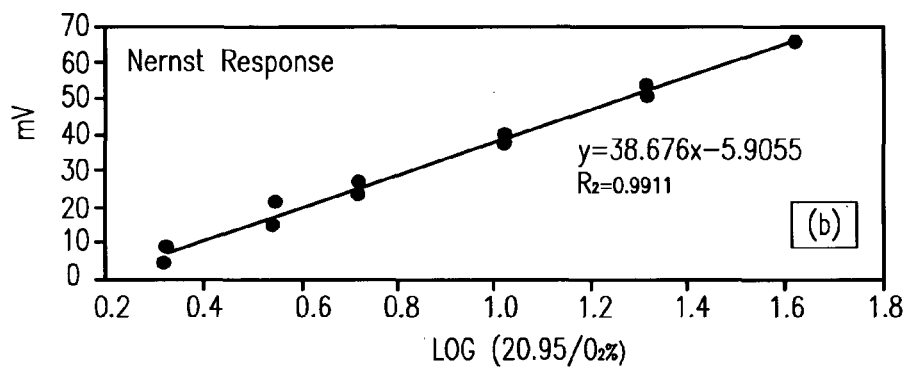
Figure 10:
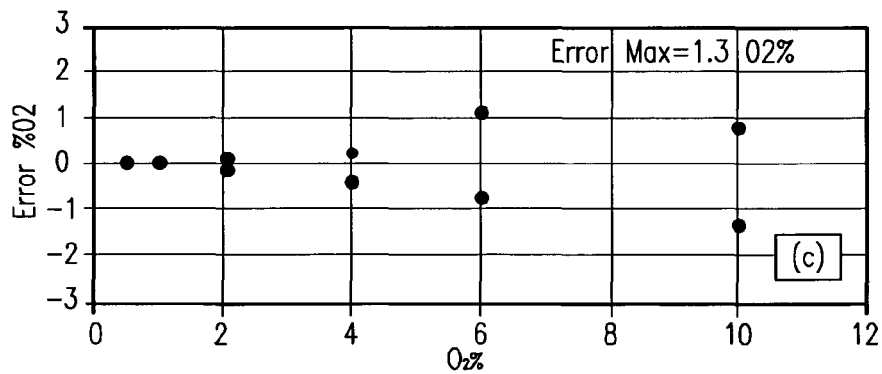
Figure 11:
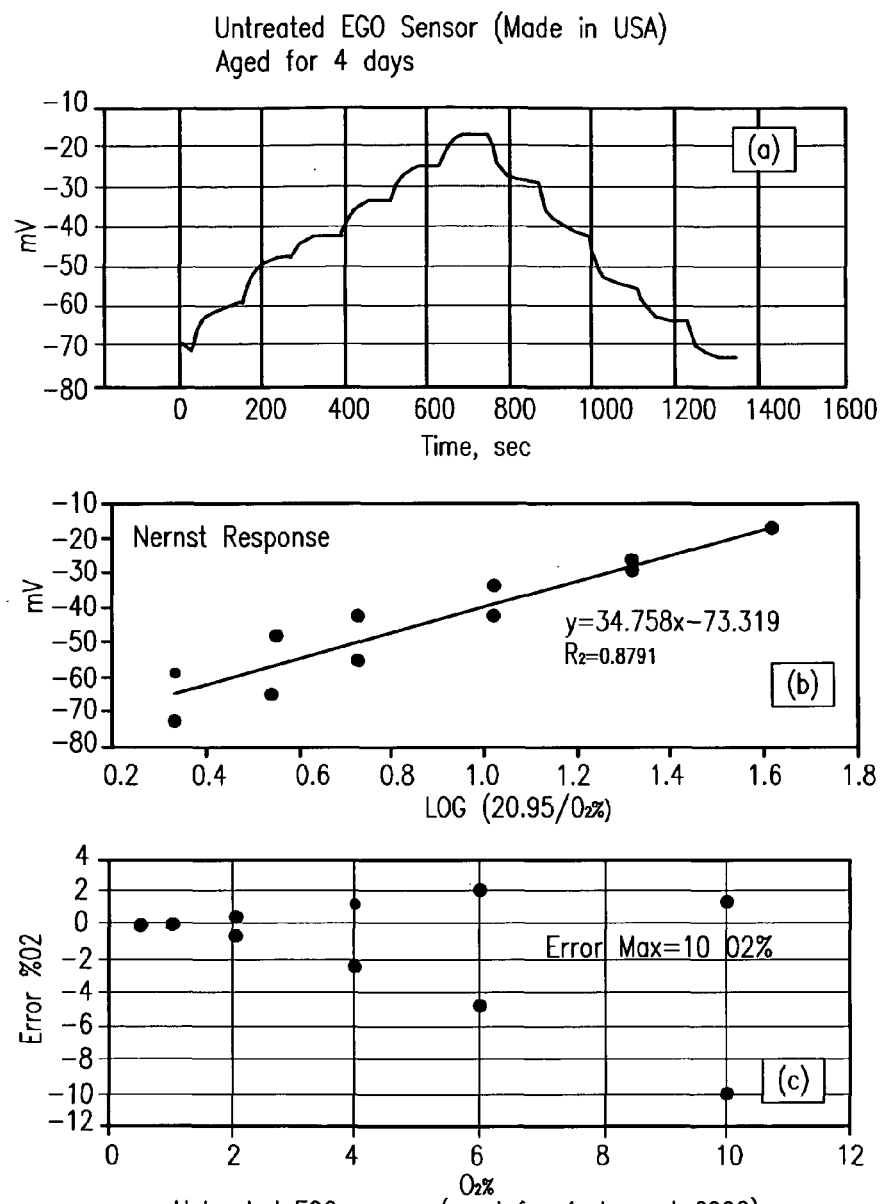
FIG. 11 shows the performance of untreated sensors untreated sensors of the type made in USA, edged for 4 days at 600° C., showing raw voltage output while subjected to oxygen step changes.
Figure 12:
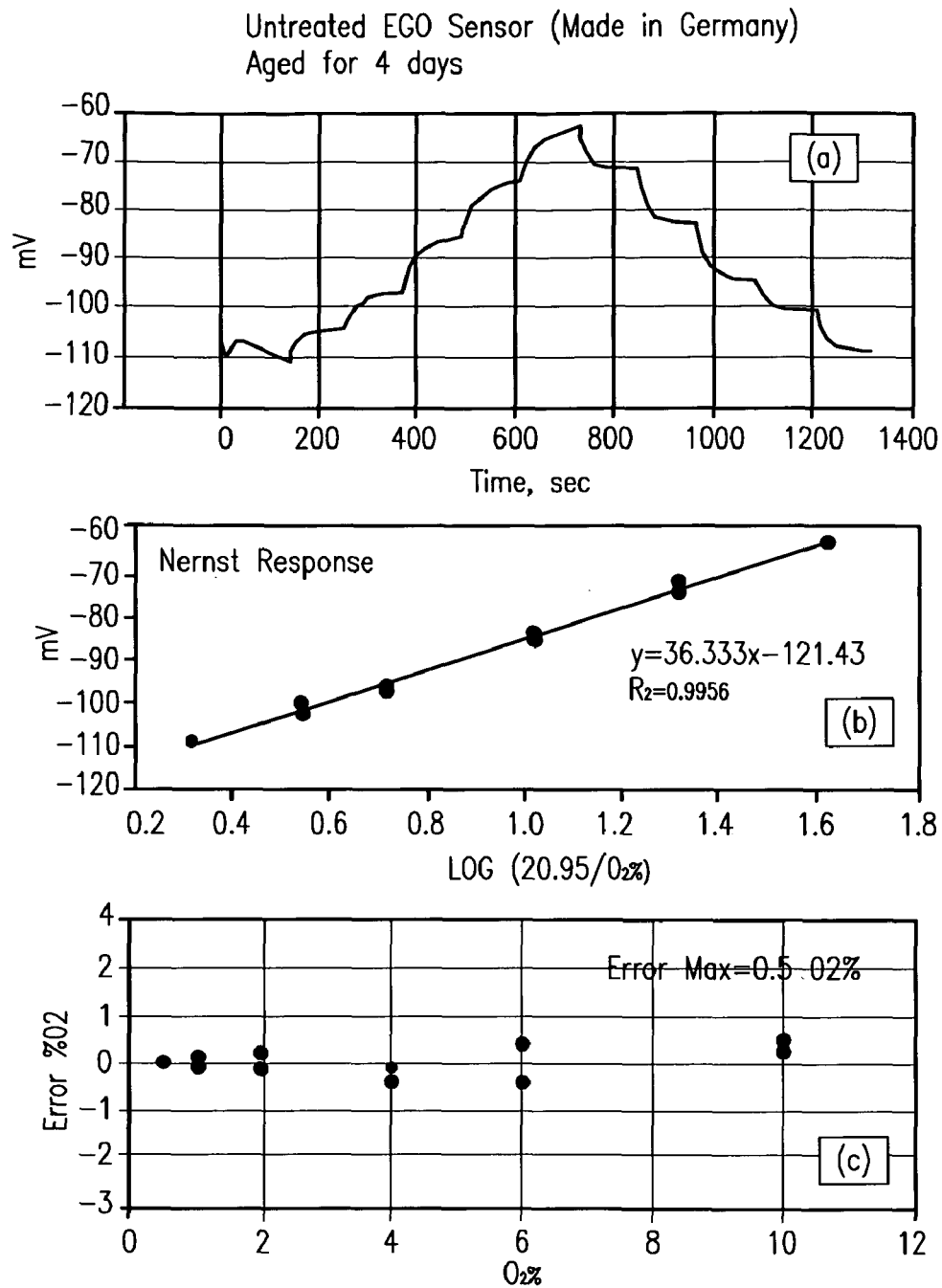
FIG. 12 shows the performance of untreated sensors of the type made in Germany and edged for 4 days at 600 C, showing raw voltage output while subjected to oxygen step change.
Figure 13:
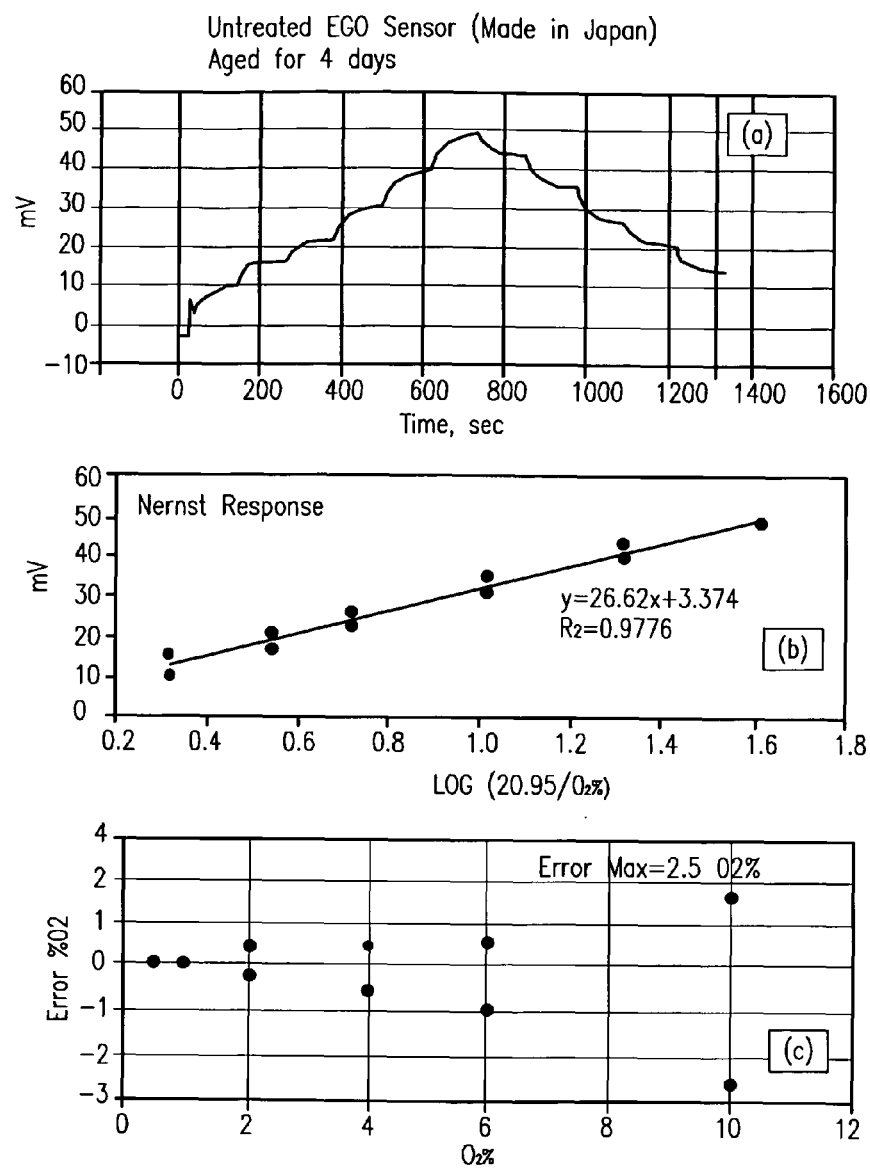
FIG. 13 shows the performance of untreated sensors of the type made in Japan, showing raw voltage output while subjected to oxygen step change.

Treated and untreated sensors were subjected to known oxygen level ambient gas streams and the sensor output was measured in each case. Measured voltages were fitted by the Nernst equation and accuracy of measurements were determined in each case. Sensors were heated with internal heaters and the ambient temperature inside the test chamber was ~500° C. From comparing FIG. 9 with FIGS. 10-13 it is clearly seen that performance of the EGO sensor treated with square wave voltage as in the present invention is significantly better than different types of untreated sensors. Measurement accuracy of the treated EGO sensor is compatible with high end commercial sensors used for industrial combustion process control. This sensor can significantly improve accuracy and reliability of the dual exhaust gas oxygen sensors systems used in automotive applications.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. By way of example, and not as a limitation, there are other applications that utilize a pair of metal electrodes separated by a gas impervious solid state ionic conductor, such as for use in zirconia membranes for gas separation/purification, or for use in fuel cells. In such applications, different metals, such as palladium, nickel, platinum/rhodium mixtures, and the like can be used as electrodes. However, since the benefits of the present invention are anticipated as being applicable to these analogous areas as well, it is intended that the scope of the invention be defined by the Claims appended hereto and their equivalents. Therefore, the scope of the invention is to be limited only by the following claims.

What is claimed is:

1. A method for improving an activation treatment of apparatus comprising of at least one member of a solid state ionic conductor supporting at least one pair of metal electrodes, wherein the improvement comprises:
   heating said apparatus from an initial temperature to a treatment temperature;
   soaking said apparatus at treatment temperature;
   cooling said apparatus to the initial temperature; and
   continuously applying a voltage of alternating polarity between said pair of electrodes in a specific ambient gas atmosphere,
   wherein voltage is applied throughout said heating, soaking and cooling period and wherein said voltage is higher than the reduction potential of said solid state ionic conductor but less than the voltage causing mechanical disintegration of said solid state ionic conductor.

2. The method of claim 1, wherein activation treatment is performed in said specific ambient gas atmosphere selected from the group consisting of: ambient atmosphere (air); reducing atmosphere; and inert atmosphere.

3. The method of claim 1, wherein said voltage is symmetrical and of alternating polarity comprises a square wave, direct current pulse performed at a frequency of less than 0.5 Hertz.

4. The method of to claim 1, wherein said voltage is symmetrical and of alternating polarity is provided as an Alternating Current (AC) at a frequency of less than 0.5 Hertz.

5. The method of claim 1, wherein said voltage is symmetrical and of alternating polarity comprises a square wave pulse, direct current pulse performed with voltage amplitude of greater than 2.4 Volts in ambient atmosphere (air).

6. The method of claim 5, wherein the amplitude of said voltage applied is greater than or equal to 2.4V.

7. The method of claim 5, wherein the amplitude of said voltage applied is less than or equal to 5.0V.

8. The method of claim 1, wherein the temperature during said soaking period is higher than the intended operating temperature of said apparatus.

9. The method of activating an electrochemical device according to claim 1, wherein said heating occurs to a temperature not greater than 1100 degrees Celsius and not less than 400 degrees Celsius.

10. A method for improving an activation treatment of apparatus comprising of at least one member of a solid state ionic conductor supporting at least one pair of metal electrodes, wherein said ionic conductor is a gas impervious, solid-state ionic conductor, and wherein the improvement comprises:
    heating said apparatus from an initial temperature to a treatment temperature;
    soaking said apparatus at treatment temperature;
    cooling said apparatus to the initial temperature; and
    continuously applying a voltage of alternating polarity between said pair of electrodes in a specific ambient gas atmosphere,
    wherein voltage is applied throughout said heating, soaking and cooling period and wherein said voltage is higher than the reduction potential of said solid state ionic conductor but less than the voltage causing mechanical disintegration of said solid state ionic conductor.

11. The method of claim 10, wherein said solid-state ionic conductor is zirconia.

12. The method of claim 10, wherein said metal coating is selected but not limited to the group consisting of: platinum; palladium, nickel, and platinum/rhodium alloys.

13. The method of claim 10, wherein said sensor apparatus forms an oxygen sensor.

14. The method of claim 10, wherein said sensor apparatus forms a gas separation and purification membrane.

15. A solid state ionic conductor product formed of the method of claim 1, wherein said sensor apparatus forms an electrochemical fuel cell.

16. The method of claim 1, wherein a symmetrical voltage of alternating polarity between said pair of electrodes is applied with sufficient amplitude to create a surface reduction of said solid state ionic conductor.

* * * * *